(12) United States Patent
Nakazato

(10) Patent No.: US 7,261,800 B1
(45) Date of Patent: Aug. 28, 2007

(54) AUTOMATIC IN SITU ELECTROPHORESIS METHOD AND APPARATUS

(75) Inventor: Tokiya Nakazato, Saitama (JP)

(73) Assignee: Helena Laboratories, Beaumont, TX (US)

( * ) Notice: Subject to any disclaimer, the term of this patent is extended or adjusted under 35 U.S.C. 154(b) by 750 days.

(21) Appl. No.: 10/648,031

(22) Filed: Aug. 26, 2003

Related U.S. Application Data

(60) Provisional application No. 60/405,980, filed on Aug. 26, 2002.

(51) Int. Cl.
*G01N 27/26* (2006.01)

(52) U.S. Cl. ............... 204/456; 204/607; 204/463; 204/613; 422/65

(58) Field of Classification Search ........... 204/457, 204/456, 461, 463, 465, 608, 606, 613, 615, 204/616, 618; 366/237, 629
See application file for complete search history.

(56) References Cited

U.S. PATENT DOCUMENTS

| | | | |
|---|---|---|---|
| 361,070 A * | 4/1887 | Long .................... | 366/237 |
| 4,360,418 A | 11/1982 | Golias | |
| 4,391,689 A | 7/1983 | Golias | |
| 4,810,348 A | 3/1989 | Sarrine et al. | |
| 4,890,247 A | 12/1989 | Sarrine et al. | |
| 4,909,920 A | 3/1990 | Sarrine et al. | |
| 4,986,891 A | 1/1991 | Sarrine et al. | |
| 5,200,045 A * | 4/1993 | Warren et al. ............... | 436/516 |
| 5,443,791 A * | 8/1995 | Cathcart et al. ............... | 422/65 |
| 5,460,709 A * | 10/1995 | Sarrine et al. ............... | 204/607 |
| 5,801,004 A * | 9/1998 | Hudson et al. ............ | 435/7.23 |
| 6,132,685 A * | 10/2000 | Kercso et al. ............... | 422/104 |
| 6,932,895 B2 * | 8/2005 | Anderson et al. ........... | 204/613 |
| 2003/0003022 A1 * | 1/2003 | Tamura et al. ................ | 422/99 |

FOREIGN PATENT DOCUMENTS

JP 09-029162 A * 2/1997

OTHER PUBLICATIONS

Machine Translation of JP 09-029162 A (Feb. 1997).*

* cited by examiner

*Primary Examiner*—Nam Nguyen
*Assistant Examiner*—Surekha Vathyam
(74) *Attorney, Agent, or Firm*—Egbert Law Offices

(57) ABSTRACT

A method of in situ electrophoresis of biological samples has the steps of preparing a sample plate and a gel plate, applying reagent onto the gel plate, moving an applicator to the sample plate so as to receive a sample onto the applicator, moving the applicator toward the gel plate such that at least a portion of the sample is loaded onto the gel plate, electrophoresing the gel plate, staining the gel plate and scanning the stained gel plate so as to electronically analyze a band in the gel of the gel plate.

34 Claims, 4 Drawing Sheets

AUTOMATIC IN SITU ELECTROPHORESIS METHOD AND APPARATUS

RELATED U.S. APPLICATIONS

The present application claims priority from Provisional Patent Application No. 60/405,980, filed on Aug. 26, 2002, and entitled "Automatic In Situ Electrophoresis Method and Apparatus".

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention is related to the field of electrophoretic analysis of biological specimens. More particularly, the present invention is directed to a method and apparatus for automatically conducting electrophoresis with an electrophoresis plate. Additionally, the present invention is related to in situ electrophoretic analysis of biological specimens.

BACKGROUND OF THE INVENTION

Electrophoresis is a scientific technique of moving charged particles, using an electric field, through solid or semi-solid media. The technique is commonly used in scientific research, including medical laboratories for analyzing various blood proteins.

In the analysis of biological material, it is known that much information can be provided by identification and qualification of certain components, such as proteins or nucleic acid fragments. It is well known that electrophoresis is an effective method of identifying the respective components of such biological material for subsequent microscopic analysis of the sample or for subsequently employing optical densitometry techniques in analyzing the samples.

In the basic method of electrophoresis, an electric field is applied across a diffusion medium. The diffusion medium contains biological particles having an electric charge. As the electric field is applied, the biological particles migrate through the diffusion medium at different rates, depending on the amount of charge on the particles and size of the particles. Thus, the biological particles are separated into distinct bands as a result of the differential migration. Subsequent staining of the fractional components in the diffusion medium allow visual analysis by optical densitometry or other methods.

Electrophoresis has been performed through a series of manual steps for many years. The manual process typically starts with preparing an electrophoresis chamber. The chamber is used to create the electric field. The chamber includes a rectangular electrically insulated container having electrodes at opposite ends thereof. The chamber is then filled with a buffer to create the interface between the two electrodes for supporting the electric field. The buffer is typically a stable aqueous solution. Next, the operator must prepare the diffusion medium, such as SDS, cellulose acetate or agarose gel. The gel is set upon a support medium, such as MYLAR™, so as to maintain the structural integrity of the gel during handling.

After the operator has prepared the electrophoresis chamber, the operator then manually applies, as precisely as possible, consistent volumes of the biological samples to precise locations in the diffusion medium or gel. The operator then places the gel into the electrophoresis chamber so that the edges of the gel are aligned with electrodes at each of the longitudinal ends of the chamber. The electric field is applied using a precise and consistent high voltage applied for a precise and consistent interval of time across the gel in the buffer solution.

After the electric field has been removed, the operator manually moves the gel into another container to apply a uniform coating of staining reagent to the surface of the gel, thus allowing a precise and consistent interval of time for the reagent and sample to chemically react. The staining reagent can be a colormetric or enzymatic solution, used to chemically combine with the bands of the biological particles of the sample, thereby causing the bands to exhibit optical characteristics. The operator may place the gel into a temperature controlled oven and incubate the gel, using a precise and consistent temperature and time interval. Incubation controls the chemical reaction between the bands and the staining reagent by means of applying heat for a fixed interval of time. The operator then dries the gel by increasing the oven temperature for a second precise and consistent temperature and time interval. The drying process stops the reaction between the bands and the reagent.

There have been prior art apparatus and methods available for automatically performing electrophoresis and staining of the plurality of samples applied to a diffusion medium. For example, U.S. Pat. No. 4,360,418 to Golias and U.S. Pat. No. 4,391,689 to Golias describe an automated electrophoresis and staining apparatus and method. Such prior art includes an electrophoresis chamber and a series of vats mounted upon a platform and arranged in a row where the vats are adapted to contain, respectively, a liquid stain and a series of plate processing solutions. The plate holder rack, having a horizontal open frame, supports an upright electrophoresis plate or support medium onto which has been applied a sample for electrophoretic fractionization. Such an electrophoresis plate had to have been previously prepared by applying samples either manually or by using one of the parallel applicators described above. The plate is nested within the chamber within an electrophoretic circuit for a predetermined time period. A power-operated lift and transfer assembly is provided on the base and is adapted to lift, transfer and lower the plate holder rack and plate from the chamber progressively into each of the underlying vats for a predetermined period of time in a linear stepping motion maintaining the plate in an upright position at all times. It is noted that the staining process relies on chemical procedures for the staining process rather than the manual system described above where incubation and drying are used.

U.S. Pat. No. 4,890,247, issued Dec. 16, 1989 to Sarrine et al., and owned by the present applicant, describes an automatic electrophoresis apparatus and method. In this patent, an electrophoresis machine is described in which all electrophoresis processing, scanning and densitometer functions are automatically performed under computer control. This machine includes an apparatus for automatically pipetting samples from the sample plate to the surface of the support strip. There is also an apparatus for applying electric current to the strip while simultaneously cooling it. Additionally, and furthermore, the device includes apparatus for applying and spreading fluorescent staining reagents to the strip. The device includes a special apparatus for incubating the strip and subsequently drying the strip. A video camera, mounted to a fluorescent scanning box which encloses the application plate, is used in combination with digital processing equipment so as to electronically scan the electrophoretically longitudinally displaced components of the samples for determining relative component densities. The subject matter of this patent is also described in U.S. Pat. Nos. 4,810,348, 4,909,920, and 4,986,891. Each of these patents is also owned by the same assignee.

U.S. Pat. No. 5,460,709, issued on Oct. 24, 1995 to Sarrine et al., also discloses another type of automatic electrophoresis method and apparatus. This apparatus is used for automatically performing medical assays and includes an electrophoresis platform which cooperates with a gantry assembly. The electrophoresis platform and the gantry assembly are movable along paths that are perpendicular to each other. An applicator assembly includes pipettes which transfer samples in a specimen tray to a electrophoresis plate mounted on the electrophoresis platform. The electrophoresis platform then moves to a position into the gantry assembly, where electrophoresis is conducted to separate the samples into different fractions. The electrophoresis platform then moves between a reagent pouring station where a reagent is applied to make the separated fractions fluoresce under ultraviolet light. The electrophoresis platform is then moved beneath the gantry assembly again as an air knife in the gantry assembly spreads the reagent. After incubation and drying of the electrophoresis plate, the electrophoresis platform and the gantry assembly are moved relative to one another while the electrophoresis plate is read with the aid of ultraviolet lamps and a photomultiplier tube mounted in the gantry assembly. The gain of the photomultiplier tube is automatically adjusted and the data gathered is automatically edited to remove background noise.

It is object of the present invention to provide an improved method and apparatus for automatically conducting electrophoresis.

It is another object of the present invention to provide an electrophoresis method whereby a single pipette can be used for the various operations associated with the gel plate and with the staining of the electrophoresed plate.

It is another object of the present invention to provide an automatic electrophoresis method and apparatus whereby all the operations are carried out in situ.

It is another object of the present invention to provide an automatic electrophoresis method and apparatus in which the de-staining operation can be carried out in a convenient and easy manner.

It is a further object of the present invention to provide an automatic electrophoresis method and apparatus which allows a plurality of reagents to be dispensed by a single pipette so that various analyses can be carried out.

It is a further object of the present invention to provide an automatic electrophoresis method and apparatus which provides a single apparatus for automatically applying a plurality of biological samples to a diffusion medium, automatically subjecting such samples to electrophoresis, automatically staining such samples, automatically incubating and drying the support medium in which the components of the samples have been separated into longitudinal bands, and automatically scanning such bands so as to automatically display results.

These and other objects and advantages of the present invention will become apparent from a reading of the attached specification and appended claims.

BRIEF SUMMARY OF THE INVENTION

The present invention is a method for in situ electrophoresis of biological samples which includes the steps of: (1) preparing samples plates, mounted gel plates on plate holders, and an applicator; (2) loading reagents into a plurality of reagent reservoirs; (3) loading a wetting agent container into a wetting agent reservoir; (4) selecting a mounted gel plate in the mounted gel plate storage and moving the mounted gel plate to an application station; (5) transferring a sample plate to the application station so as to be positioned adjacent to the mounted gel plate in the application station; (6) moving an applicator to the applicator loader for loading thereon; (7) moving the applicator into the sample plate so as to receive a sample thereon; (8) moving the applicator such that the sample is applied into the mounted gel plate; (9) moving the applicator to a used applicators case for unloading thereon; (10) applying the wetting agent to a cooling plate of the electrophoresis chamber to promote complete contact between the mounted gel plate and the cooling plate; (11) electrophoresing the sample-containing mounted gel plate; (12) drying the electrophoresed mounted gel plate; (13) staining the dried electrophoresed mounted gel plate; (14) de-staining the stained electrophoresed mounted gel plate; (15) drying the stained electrophoresed mounted gel plate; (16) scanning the dried stained mounted gel plate so as to electronically analyze the visible band in the gel; and (17) disposing of the scanned mounted gel plate.

In the present invention, the sample plates and the gel plates are initially stacked into the housing of the electrophoresis apparatus. The sample plates are loaded manually in a conventional fashion. The sample plates will include a plurality of sample wells formed on a single sample plate. Similarly, the reagents can be loaded into the plurality of reagent reservoirs in a manual fashion. The present invention utilizes a plurality of reagent reservoirs so that different reagents can be used for different testing methodology or for the storage of additional similar reagents for multiple tests.

Initially, a plate holder is used to mount a gel plate for testing. The plate holder has a frame and electrodes. The mounted gel plate is moved from the mounted gel plate storage to the application station. A single pipette is provided so as to be in communication for loading with the wetting agent in the wetting agent container. The pipette is inserted into transfer hole in the electrophoresis station so as to apply the wetting agent onto the cooling plate of the electrophoresis chamber which is equipped with a cooling device. The mounted gel plate is then conveyed from the application station to the cooling plate in the electrophoresis station.

The sample plates are initially stacked on a side of the housing of the present invention opposite from the stacking of the gel plates. A single sample plate is conveyed along the front track so as to be positioned forward of the gel plate in the application station.

The applicator includes a plurality of application elements which correspond in location to the respective plurality of samples wells formed on the sample plate. The applicator, along with its plurality of application elements, will be shuttled on a gantry so as to be positioned directed above the sample wells. The applicator is then lowered so that the application elements of the applicator are inserted into the respective sample wells of the sample plate. Each of the samples will be adhesively received on the end of each of the application elements. The applicator is then lifted such that the plurality of application elements are removed from the respective plurality of sample wells with the samples retained respectively on each of the application elements. The applicator is then shuttled so as to be in position above the gel plate. The applicator is then lowered such that the application elements will enter the gel of the gel plate. The applicator is then lifted again so that the samples are retained within the gel plate.

The electrophoresing of the sample-containing mounted gel plate is carried out in a conventional manner such as described in the prior art patents to the present assignee. The apparatus of the present invention closes the electrophoresis chamber such that the electrodes in the gel on the mounted gel plate will contact a power source. An electric field will then be applied to the mounted gel plate for the purpose of electrophoresing the sample-contained gel plate. The cooling plate of electrophoresis chamber is also lifted to promote complete contact between the gel plate and is maintained in cool.

In the present invention, the electrophoresed mounted gel plate is properly stained. However, in present invention, a single pipette is used for the staining operations associated with the mounted gel plate. Initially, the electrophoresed mounted gel plate is moved to a staining station. The pipette is filled with a proper reagent. In particular, the reagent in one of the plurality of reagent reservoirs will be in fluid communication with the pipette so as to fill the interior of the pipette with the appropriate reagent. The pipette is then moved on the gantry to a position above a roller located in the staining station. The pipette and roller positioned over staining window located above the mounted gel plate. The staining reagent is released from the pipette onto the roller. The roller will roll across the mounted gel plate so as to spread the staining reagent across the surface of the gel plate. Alternatively, the electrophoresed mounted gel plate is conveyed from the electrophoresis chamber to a dryer before being conveyed to a staining station.

In the present invention, the stained electrophoresed gel plate is properly dried by air drying or by oven drying. In particular, the stained gel plate is moved to a drying station. In one form of the present invention, the stained gel plate is dried by blowing heated air across the surface of the plate. Alternatively, the stained gel plate can be incubated in other conventional ways. Where heated air is used, the distances between the heated air source and the gel plate can be properly adjusted to the desired drying characteristics.

The dried mounted gel plate can then be moved to a scanning station so that as to electronically analyze the visible bands in the gel. This scanning operation will measure the location, intensity, resolution of the band and the gel plate number printed on gel plate so as to create a profile for the identification of the sample. The scanned information can be displayed on a computer terminal or can be printed out by known techniques. The scanned mounted gel plate then can be properly disposed of by moving the scanned mounted gel plate from the scanning station to a disposal station. The scanned mounted gel plates can then be stacked from the bottom to the top in a location opposite to that of the application station.

In the present invention, since a single pipette is used, the pipette must be washed subsequent to the step of applying the reagent in the electrophoresing station and also subsequent to the staining. In each case, the pipette is washed by aligning the pipette with a water wash, filling the interior of the pipette with water, and also by placing the pipette into a water rinse so as to wash the exterior of the pipette. The tip of the pipette can then be blotted onto blotter paper and the interior of the pipette aspirated. As a result, the pipette will suitable cleaned for the receipt of other reagents therein or for use in association with further analysis.

In the present invention, the roller is also washed subsequent to the staining. The washing of the roller involves the step of moving the roller to a roller wash station, lowering the roller so as to be submersed in water, and then rolling the roller over a blotter paper so as to release water from the roller and to dry the roller.

The present invention also involves the unique step of de-staining the dried mounted gel plate or the incubated mounted gel plate prior to the step of scanning. In those circumstances where de-staining is required, the stained mounted gel plate is moved from the drying or the incubating station to a washing station. The mounted gel plate is moved to the de-staining or washing station, wherein washing or fixing liquid is kept in the plate holder. As one end of the plate holder acts as a pivot, the plate holder is tilted at angle. A flow of washing or fixing liquid is then applied across the tilted mounted gel plate such that the flow of the washing or fixing liquid flows from the raised end of the mounted gel plate to the lowered end of the mounted gel plate. The surface of the mounted gel plate is suitably wiped so as to agitate the washing or fixing liquid flow across the surface of the tilted mounted gel plate. The de-stained mounted gel plate can then be leveled so as to have a horizontal orientation. This de-stained gel plate can then be moved to a station for drying, and the de-stained mounted gel plate can be moved to the scanning station for analysis. In the present invention, the back side of mounted gel plate is also washed by flowing of the washing or fixing liquid between the plate holder and the back side of mounted gel plate.

BRIEF DESCRIPTION OF THE SEVERAL VIEWS OF THE DRAWINGS

FIG. 2(*b*) is a top plan view of a mounted gel plate. FIG. 2(*c*) is a side view of the mounted gel plate in the plate holder.

DETAILED DESCRIPTION OF THE INVENTION

Figure 1:
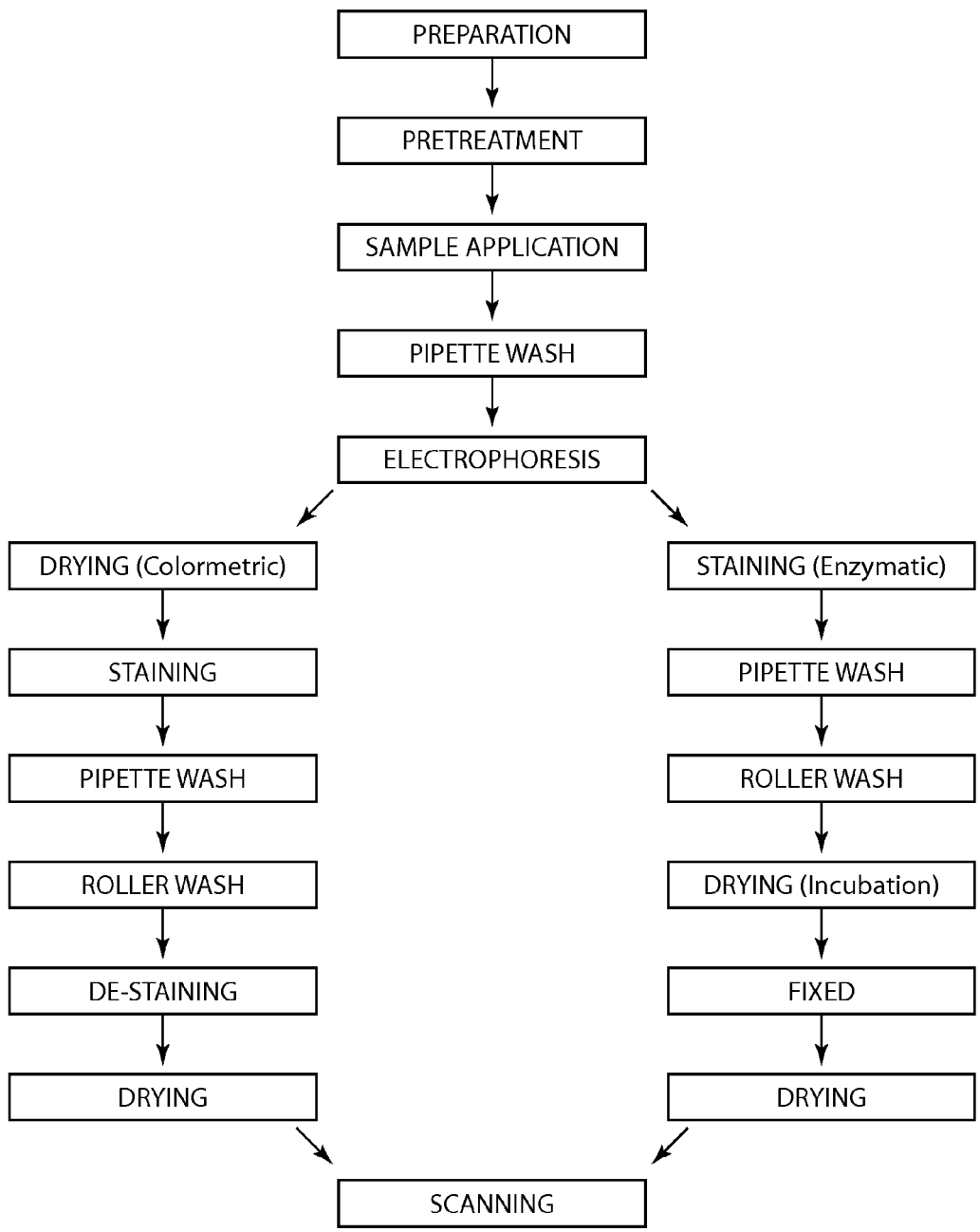
FIG. 1 is a block diagram showing the operation of the present invention.

Referring to FIGS. 1-5, the various steps associated with the automated electrophoresis apparatus method of the present invention are particularly illustrated. FIG. 1 shows a block diagram of the operations of the present invention, while FIGS. 2-5 show the structures associated with the apparatus for performing the steps as shown in FIG. 1.

Figure 4:
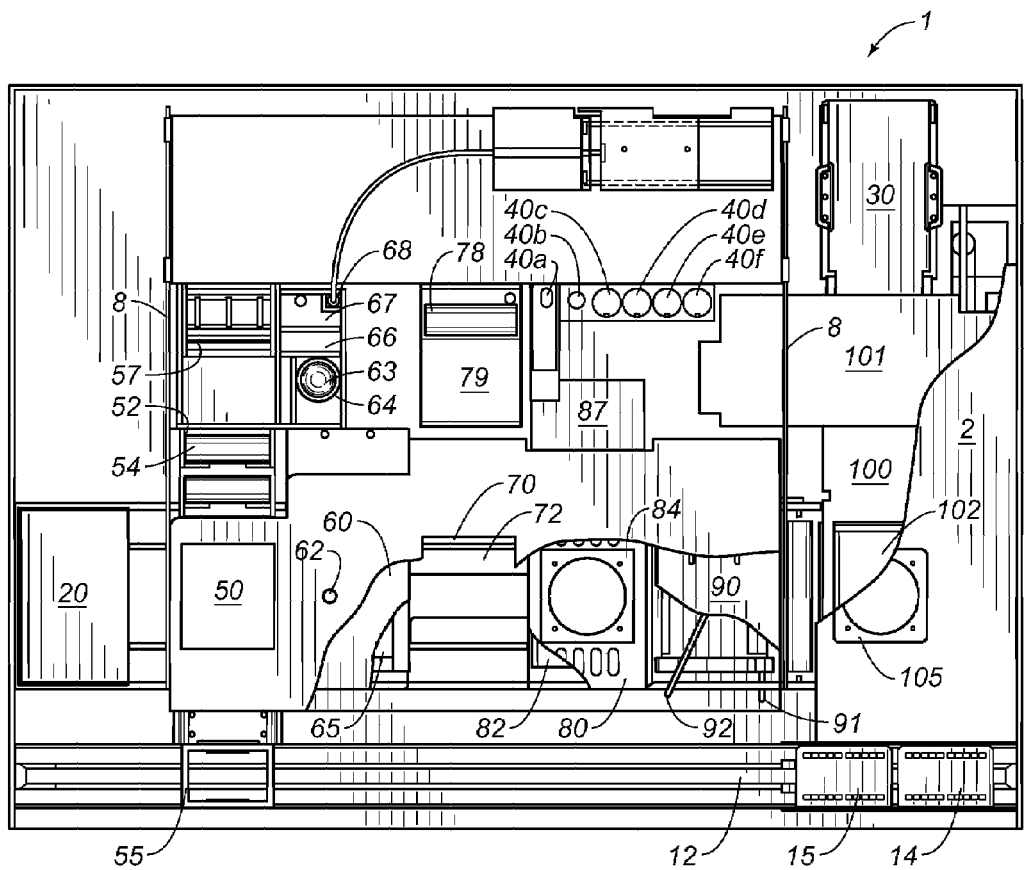
FIG. 4 is a top plan view, having a partially excluded top cover showing the various stations associated with and positioned within the apparatus of the present invention.
Figure 5:
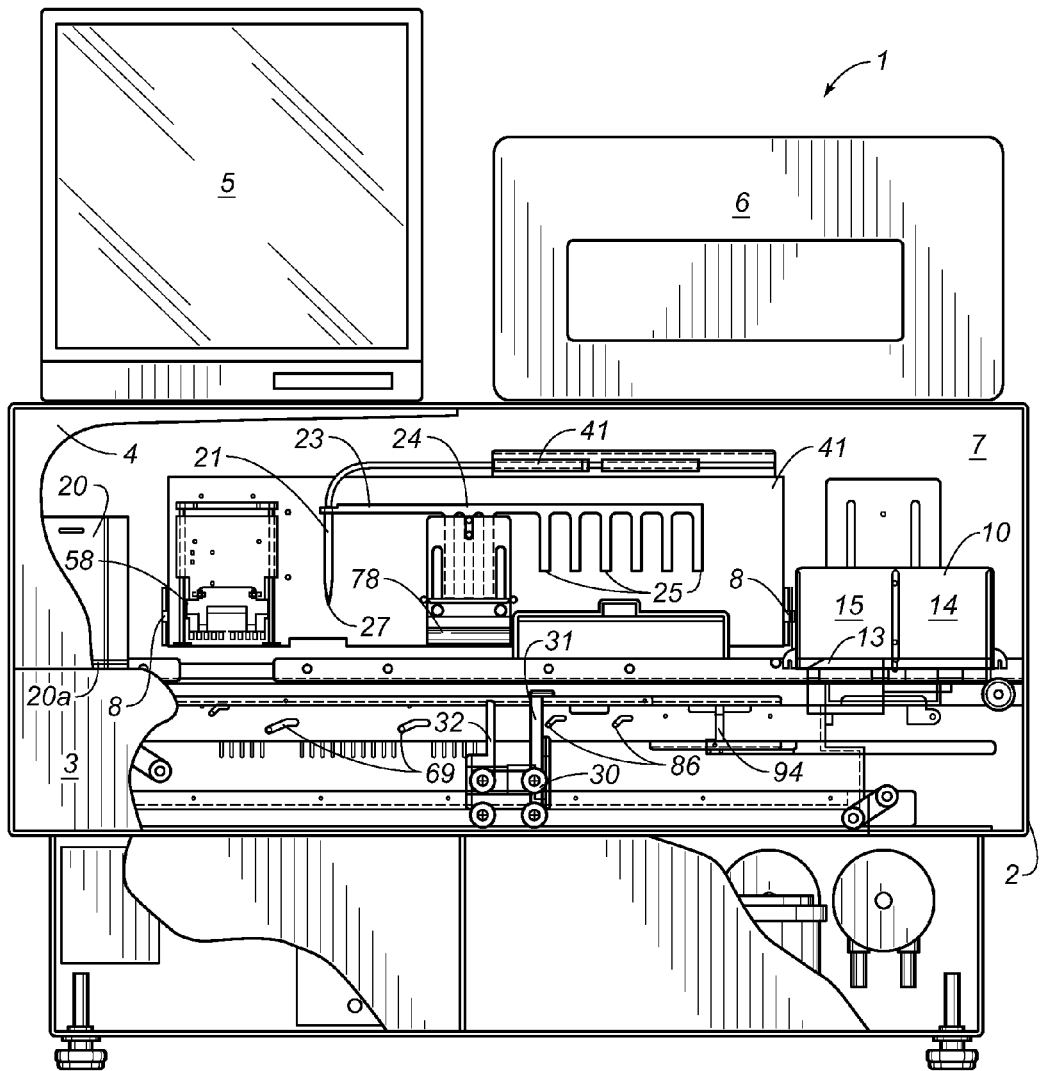
FIG. 5 is a front elevational view, having a partially excluded front cover showing the apparatus of the present invention and the stations associated therewith and positioned therein.

Referring to FIGS. 4-5, the automatic electrophoresis apparatus of the present invention is particularly illustrated. The apparatus 1 includes a housing 2 which generally surrounds the various components associated with apparatus of the present invention. In FIG. 5, in particular, the apparatus 1 includes a base 3 which supports each of the components thereon. As can be seen in FIG. 5, a computer terminal 5, and printer 6 can be used for the purpose of receiving the analyzed information from the interior of the cover 4 and for controlling the operation of the various components located within the interior of the housing 2 of the automated electrophoresis apparatus 1.

Figure 2A:
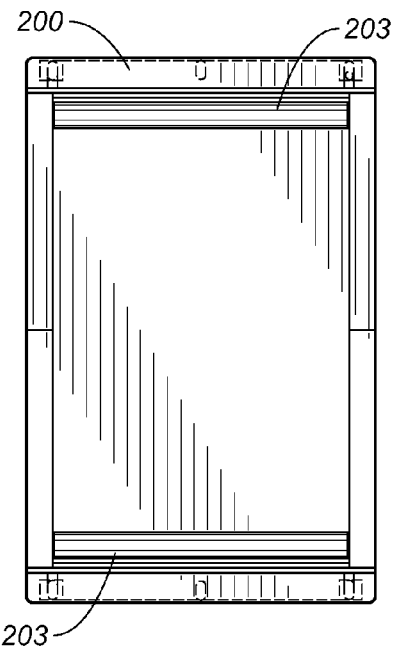
FIG. 2(*a*) is a top plan view of a plate holder.
Figures 2B, 2C:
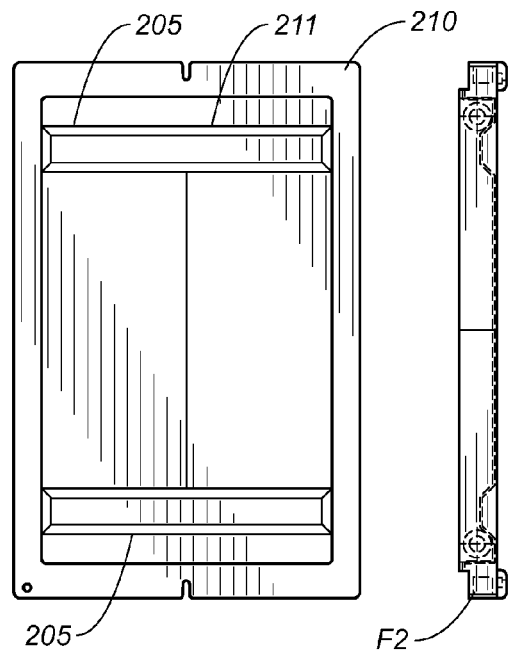
Figure 3:
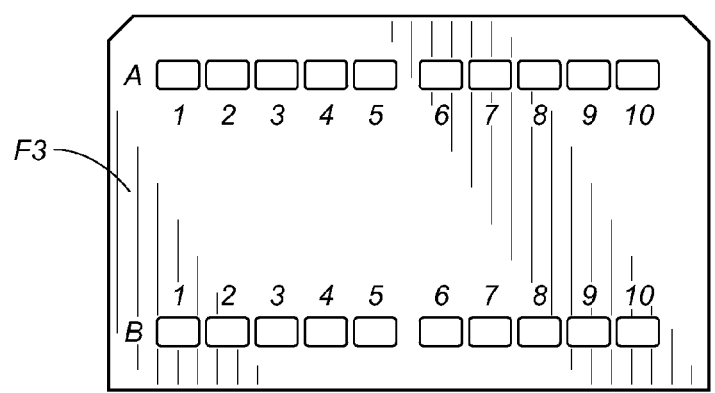
FIG. 3 is a top plan view of the sample plate of the present invention, having numbered wells.

In FIG. 1, it can be seen that the very first step associated with the method of the present invention is the preparation of the sample plates, the mounted gel plates and the reagents. Initially, the manually loaded sample well plates are placed into the sample plate storage 10 located at the right side of the housing 2 of the automated electrophoresis apparatus 1. FIG. 3 shows a top plan view of a sample plate F3, having numbered wells. This example of a sample plate may be used in the present invention. The mounted gel plates are loaded into the mounted gel plate storage 20 located on the opposite side of housing 2. FIGS. 2(a-c) show the structures of a mounted gel plate F2, comprised of a plate holder 200, electrodes 203 and a gel plate 210. The plate holder 200 protects the gel plate from evaporation when placed in the mounted gel plate storage 20, the electrophoresis chamber, the incubator and the de-staining compartment. The appropriate reagents used for the electrophoresis operation of the present invention are placed in the respective reagent reservoirs 40a-40f. Once the sample plates are loaded in the sample plate storage 10, the gel plates are loaded into the mounted gel plate storage 20 and the reagents are appropriately loaded, the automated electrophoresis apparatus 1 of the present invention will be able to carry out a large number of analyses in situ. As a result, contamination of samples is effectively avoided. Similarly, the human element associated with the manipulation of the electrophoresis analysis technique is avoided. The present invention carries out each of the steps in an automated manner so that the results can be displayed on the computer screen of computer 5 or printed out by printers 6.

The preparation of the sample plate F3 and the mounted gel plate F2 includes lowering the bottom 20a of the mounted gel plate storage 20 so as to release the mounted gel plate F2 selected for testing. The single selected mounted gel plate F2 is moved from the gel plate storage 20 to the application station 50. Similarly, a single sample plate F3 is moved from the waiting stock 14 in the sample plate storage 10 by transferring belt 11. Before the transfer belt 11 is operated, the bottom 13 of the finished stock 15 is lifted so as to make space for passing the sample plate F3 under the finished stock 15. Then, the single sample well plate F3 is transferred into the position of sample well plate holder 55 by transfer belt 11.

As can be seen in FIG. 5, the pipette 21 is movably received within a slot 23 formed on the gantry 61. Each of the reagent reservoirs 40a-40f are located within respective slots 25 communicating with slot 23 and formed on the gantry 61. Suitable servomotors or stepper motors can be connected to mechanisms within the gantry 61 so as to automatically control the movement of the pipette 21 from a position associated with one of the reservoirs 40a-40f to a desired dispensing position.

Preparation of the wetting agent 63 is the next pretreatment step. A wetting agent 63 is only one type of pretreatment reagent that may be used in the present invention. A pipette 21 controlled by syringe 41 transfers a drop of the wetting agent 63 from the wetting agent vials 64 onto the cooling plate 65. In particular, the pipette 21 will be moved so as to be inserted into the transfer hole 62 in the electrophoresis station 60 in order to release the drop of the wetting agent 63 on to the cooling plate 65.

Subsequent to dispensing the wetting agent 63 on the cooling plate 65, the gantry 61 will move the pipette 21 so as to align the pipette 21 with the water rinse 68 (illustrated in FIG. 4) so that water can be released from the water rinse 68 to clean the outside of the pipette 21 in the dispensing spot 67. The dispensing water rinse 68 will suitably inject water into the interior of pipette 21 so as to clean the interior of the pipette. The tip of the pipette 21 can be dried by blotting the tip 27 of the pipette 21 on blotter paper 66. Additionally, if necessary, an air source can be applied to the pipette 21 so as to suitably aspirate any remaining liquids or fluids from the interior of the pipette 21.

The next step in the process associated with the automated electrophoresis apparatus 1 is sample application. A sample loader 56 on the gantry 61 positions the applicator 54 from the applicator tray 52. Then gantry 61 is moved to an application site which has been previously set by computer 5. The sample plate holder 55 conveys the sample plate under the sample loader 56. The sample loader 56 on the gantry 61 positions the applicator 54 above the sample plate. The applicator 54 will have a plurality of application elements extending downwardly therefrom. Similarly, the sample plate will have a plurality of sample wells formed therein. Each of the application elements of the applicator 54 will correspond respectively with the plurality sample wells. The sample loader 56 will lower the applicator 54 into the sample well of the sample plate and then will raise the applicator 54 therefrom. The sample plate holder 55 returns to a wait site. The samples from sample wells of the sample plate are retained on the ends of the application elements associated with applicator 54 by surface adhesion. The sample loader 56 will then position the applicator 54 above the mounted gel plate. The applicator 54 is then lowered so that the sample on each of the application elements of the applicator 54 are placed into the gel on the mounted gel plate. The applicator holder 56 will then rise. Multiple applications can also be performed in the same manner. The bottom 13 of the finished stock 15 is lowered down, and the sample plate in the sample plate holder 55 is conveyed back to the finished stock 15 in the sample plate storage 10 by the front track belt 12.

Subsequent to the placement of the sample into the gel of the mounted gel plate F2, the mounted gel plate F2 is then conveyed to the electrophoresis station 60. The electrophoresis station 60 will work in a similar manner to that of the before-mentioned patents of the present assignee. A suitable conveyer is used so as to move the mounted gel plate to the electrophoresis station 60. The chamber door of the electrophoresis station 60 will be closed so that the electrodes in the gel will contact a power source in order apply the electric field. No buffer solution will be required because of prepared buffer ridge 205 on the gel plate 210. Eventually, the cooling plate 65, controlling the temperature of the electrophoresis chamber 60, was lifted to promote complete contact between the gel plate for using the wetting agent 63 and is maintained cool. The duration and the intensity of this electrical field is suitably monitored by the computer 5.

The next step of the present invention involves either the colormetric staining or the enzymatic staining of the mounted gel plate. When colormetric staining is desired, the mounted gel plate is conveyed from the electrophoresis station 60 to the staining station 70 having staining window 72. The pipette 21 is filled with a staining reagent from reagent reservoir 40b (or any of the other reagent reservoirs, as desired). The pipette 21 is then moved by gantry 61 to a position above the roller 78 located in the staining station 70. The gantry 61 will position the pipette 21 and the roller 78 over the staining window 72 above the mounted gel plate. The gantry 61 can move on the gantry rails 8. The pipette 21 will release the staining reagent onto the roller 78 as the gantry 61 lowers and moves the rollers 78 across the mounted gel plate. This rolling action will spread the staining reagent across the gel surface. Alternatively, other colormetric staining procedures can be used. For example, a drying step may precede the staining, wherein the mounted gel plate is conveyed from the electrophoresis station 60 to a drying station 80. The gel plate is dried and then conveyed from the drying station 80 to the staining station 70 for the previously described colormetric staining.

If enzymatic staining desired, then somewhat similar operations will occur. Initially, the mounted gel plate is conveyed to the staining station 70. The pipette 21 can be filled with an immunostaining or enzymatic reagent from the reagent reservoir 40c. The pipette 21 is moved to a position above the roller 78 in the staining station 70. The pipette will release the enzymatic reagent onto the roller 78 as the gantry lowers and moves the roller 78 across the mounted gel plate. This rolling action will spread the reagent across the gel surface.

In the processes associated with either the colormetric staining or with enzymatic staining, there must be a pipette wash and a roller wash. The operations associated with the pipette wash and with the roller wash will be the same for either the colormetric staining or with enzymatic staining procedures. With respect to the pipette wash, the pipette 21 will be aligned with the water rinse 68. As a result, the pipette 21 is filled with water. The pipette 21 is then is moved to the electrophoresis station 60 and the gantry 61 over the dispensing spot 67 so that water is released thereon. The water rinse 68 and the dispensing spot 67 are repeated so as to clean the outside and the inside of the pipette 21. The tip 27 of the pipette 21 can be dried by blotting the tip 27 of the pipette 21 on the pipette blotter 66.

The pipette 21 on the gantry moves to reagent development slot 24 and lowers so that the roller 78 will be submersed in water. The roller 78 is washed with water. The roller 78 is then moved over the roller blotter 79 so that water is released. The roller 78 is lowered by the pipette 21 and then dried by blotting.

The present invention allows different types of drying operations to occur depending on whether colormetric staining is involved or enzymatic staining is involved. In the case of colormetric staining, the mounted gel plate is moved to the drying station 80. A heat block 82 is located above the drying station 80. The heat block 82, having a controlled temperature, can utilize a blower or a fan 84, or other heating means so as to dry or to react the staining agent, depending upon the type of staining agent used. A heat block lift actuator 86 is incorporated so as to raise or lower the mounted gel plate to adjust contact with the heat block or the heat applied thereto.

Next, a de-staining procedure is required. Initially, the mounted gel plate is moved to the wash station 90. This wash station 90 is covered by a metal plate on the top thereof. As one end of the mounted gel plate is pivoted at fulcrum 91, a vertically controlling actuator 94 will move the slide rod 92, which will raise or lower an end of the mounted gel plate so as to control a tilt of the mounted gel plate. At least one end of the mounted gel plate is lowered so that the mounted gel plate is tilted within the wash station 90. The washing or fixing liquid source spreads water across the mounted gel plate to clean the mounted gel plate of the staining solution. A slide rod 92 will swish back and forth across to the mounted gel plate to agitate and to clean the gel plate. The back side of mounted gel plate is also washed by flow of the washing or fixing liquid between the plate holder and the back side of mounted gel plate. The de-stained gel in the mounted gel plate is now returned to the straight horizontal level orientation.

If enzymatic staining is used, then the mounted gel plate is also moved to the drying station 80. The heat block 82 will be located above the mounted gel plate. The heat block 82, fan 84 or other heating means is used to incubate and react the immunostaining or enzymatic reagent, depending on the type of reagent used. Greater temperatures may be required for the proper enzymatic reaction to occur between the sample and the gel and the newly added enzymatic agent. The heat block lift actuator 86 will serve to raise or lower the mounted gel plate to adjust contact to the heat block or the heat applied thereto. A slide cover 87 is closed over the plate holder 200 for maintaining humidity.

The final step associated with the automatic electrophoresis operation of the present invention is the step of scanning. This step of scanning applies to either of the staining processes. Initially, the mounted gel plate is moved the scan station 100. Scan station 100 has a scanner, a dryer 105 and utilizes a fan and a heat source. The mounted gel plate will, at this time, be showing visible bands. The scan station 100 will include a scanner 102 to electronically analyze the visible bands in the gel. This analysis will involve measuring the location, intensity and resolution of the bands. The collected information including the gel plate number 211 printed on the gel plate will create a profile of bands so as to allow the identification of the sample. The method of analyzing the visible bands in the gel is described in greater detail in association with U.S. Pat. No. 5,460,709 or 4,890, 247, owned by the present assignee. The mounted gel plate is then moved to the mounted gel plate disposal unit 30. This mounted gel plate disposal unit 30 will collect and stack the mounted gel plates after the scanning process has occurred. The mounted gel plates will be stacked from the bottom to the top at the side of the base 3 opposite the mounted gel plate storage 20. The scanned information can be displayed on the computer terminal 5 or printed out by way of printer 6.

In the present invention it can be seen that the mounted gel plates will move in an automated manner across the base 3 of the automatic electrophoresis apparatus 1. With reference to FIG. 5, the mounted gel plates are properly prepared on the left side of the base 3. These mounted gel plates will be passed through the various process until they are disposed on the right side of the base 3. The various other components of the automated electrophoresis apparatus will interact with these mounted gel plates as they move from station to station. The mounted gel plate is conveyed by the mounted gel plate carrier which is cached with both sides of the holder catcher 31. The cooling plate is lifted by moving the cooling plate lift 69 with the lifter 32 of the mounted gel plate carrier 33. The heater 82 is also lifted by moving the heat block lift actuator 86 with the mounted gel plate carrier 33.

Importantly, in the present invention, only a single pipette is used. As a result, the present invention avoids the problems associated with the use of multiple pipettes and coordination of movement associated therewith. The single pipette is used not only for the purpose of dispensing stain onto the roller 78 but also for the purpose of pretreating the mounted gel plate. A variety of reagent reservoirs can be utilized with the apparatus 1 of the present invention so that various types of reagents can be used for different analysis or so that an adequate supply of a particular reagent can be utilized.

The foregoing disclosure and description of the invention is illustrative and explanatory thereof. Various changes in the details of the illustrated construction or in the steps of the described method can be made within the scope of the appended claims without departing from the true spirit of the invention. The present invention should only be limited by the following claims and their legal equivalents.

I claim:

1. A method of in situ electrophoresis of biological samples comprising:
    preparing a sample plate and a gel plate, said sample plate being moved from a sample plate storage area in a first direction, said gel plate being moved from a gel plate storage area in a direction opposite said first direction to an application station;
    applying reagent onto said gel plate;
    moving an applicator to said sample plate so as to receive a sample onto said applicator;
    moving said applicator toward said gel plate such that at least a portion of said sample on said applicator is loaded onto said gel plate, said sample plate being moved to a used sample plate storage area, the sample-loaded gel plate being moved to an electrophoresis station adjacent said application station;
    electrophoresing the sample-loaded gel plate, the electrophoresed gel plate being moved to a staining station adjacent said electrophoresis station;
    staining the electrophoresed gel plate, the stained gel plate being moved to a scanning station adjacent said staining station; and
    scanning the stained gel plate so as to electronically analyze a band in the gel of said gel plate, the scanned gel plate being moved to a gel plate disposal unit.

2. The method of claim 1, wherein said sample plate is in a removable stacked relationship with a plurality of sample plates in said sample plate storage area, said sample plate being moved from a bottom of said plurality of sample plates, and wherein said gel plate is in a removable stacked relationship with a plurality of gel plates in said gel plate storage area, said gel plate being moved from a bottom of said plurality of gel plates.

3. The method of claim 1, said step of applying said reagent comprising:
    loading a plurality of reagents into a respective plurality of reagent reservoirs;
    positioning a pipette in proximity to at least one of said plurality of reagent reservoirs, said pipette being a single pipette;
    loading said pipette with said reagent;
    transferring said reagent from said pipette onto said gel plate, said pipette being moved from said proximity to the reagent reservoirs to said gel plate at said application station; and
    washing said pipette subsequent to the step of transferring the reagent from said pipette.

4. The method of claim 3, said step of washing comprising:
    aligning said pipette with a water wash;
    flushing an interior of said pipette with water;
    rinsing an exterior of said pipette with water;
    blotting a tip of said pipette so as to remove water therefrom; and
    aspirating said interior of said pipette.

5. The method of claim 1, said step of preparing the sample plate comprising forming a plurality of sample wells on the sample plate, said step of moving said applicator into said sample plate comprising:
    conveying said sample plate so as to be adjacent said gel plate; and
    lowering said applicator into at least one of said plurality of sample wells on said sample plate such that the sample is adhesively secured to said applicator.

6. The method of claim 5, said applicator comprising a plurality of applicator elements, said plurality of applicator elements correspond respectively to said plurality of sample wells, said step of lowering comprising:
    lowering said plurality of applicator elements into said plurality of sample wells on said sample plate such that each of said plurality of applicator elements receives the sample from a separate sample well on said sample plate.

7. The method of claim 1, said step of moving said applicator to said gel plate comprising:
    positioning said applicator above said gel plate;
    lowering said applicator into the gel of said gel plate such that the portion of said sample is retained by the gel; and
    lifting said applicator away from said gel plate.

8. The method of claim 1, said gel plate having electrodes formed thereon, said step of electrophoresing comprising:
    conveying the sample-loaded gel plate to an electrophoresis device;
    connecting said electrodes of said gel plate to a power source; and
    applying an electrical field to said gel plate.

9. The method of claim 1, said step of staining comprising:
    applying a staining reagent onto a surface of the electrophoresed gel plate.

10. The method of claim 9, said step of applying said staining reagent comprising:
    loading a pipette with said staining reagent;
    dispensing said staining reagent from the loaded pipette onto a roller; and
    spreading the said staining reagent across the electrophoresed gel plate by moving said roller across the electrophoresed gel plate.

11. The method of claim 10, said pipette being a single pipette, said step of applying said staining reagent further comprising:
    conveying the electrophoresed gel plate to a position below said pipette;
    moving the loaded pipette to a position above said roller; and
    positioning the staining reagent-dispensed roller over a staining window above the electrophoresed gel plate.

12. The method of claim 10, further comprising:
    washing said roller subsequent to said step of spreading said staining reagent.

13. The method of claim 12, said step of washing said roller comprising:
    moving said roller to a washing station having a water container;
    lowering said roller into said water container;
    rolling said roller so as to release the water therefrom; and
    drying said roller.

14. The method of claim 1, further comprising:
    drying the staining reagent gel plate prior to said step of scanning.

15. The method of claim 14, said step of drying comprising:
moving the stained gel plate to a drying station; and
oven drying the stained gel plate.

16. The method of claim 14, said step of drying comprising:
conveying the stained gel plate to a drying station; and
air drying the stained gel plate.

17. The method of claim 1, further comprising:
destaining the stained gel plate prior to said step of scanning.

18. The method of claim 17, said step of destaining comprising:
lowering one end of the stained gel plate such that the stained gel plate is tilted at an angle;
flowing water across a surface of the stained gel plate such that water flows from an elevated end of the stained plate toward the lower end of the stained gel plate; and
wiping the surface of said gel plate so as to remove staining therefrom.

19. The method of claim 1, said step of scanning comprising:
measuring a location and an intensity and a resolution of the band so as to create a profile for sample identification; and
displaying the profile on a display screen.

20. The method of claim 1, wherein the scanned gel plate is in a removable stacked relationship with a plurality of used scanned gel plates in said gel plate disposal unit, the scanned gel plate being stacked from a bottom of said plurality of used scanned gel plates.

21. An apparatus for in situ electrophoresis of biological samples comprising:
a housing;
a sample plate; a moving means positioned on said housing for moving said sample plate from a stacked relationship in a sample plate storage area to an application station and to a used sample plate storage area within said housing;
a gel plate, being moved from a stacked relationship in a gel plate storage area to gel plate disposal unit, said sample plate being moved anti-parallel to said gel plate within said housing;
a reagent dispensing means positioned on said housing, said reagent dispensing means being cooperative with said gel plate for applying a reagent onto said gel plate at said application station;
an applicator means positioned on said housing and cooperative with said sample plate and with said gel plate for loading a sample from said sample plate onto said gel plate at said application station;
an electrophoresing means positioned in said housing for electrophoresing the sample-loaded gel plate at an electrophoresis station, said electrophoresis station being located adjacent said application station, the sample-loaded gel plate being moved laterally to said electrophoresis station from said application station;
a staining means positioned in said housing for staining the electrophoresed gel plate at a staining station, said electrophoresis station being located between said application station and said staining station, the electrophoresed gel plate being moved laterally to said staining station from said electrophoresis station; and
a scanning means cooperative with said housing for scanning the stained gel plate to electronically analyze a band in the gel of said gel plate at a scanning station, said staining station being located between said electrophoresis station and said scanning station, the stained plate being moved laterally to said scanning station from said staining station, said gel plate disposal unit being located adjacent to said scanning station.

22. The apparatus of claim 21, said housing having a conveyer movably positioned thereon, said housing having a gantry supported thereon generally above said conveyer, said reagent dispensing means, said applicator means, and said staining means being connected to said gantry.

23. The apparatus of claim 21, said reagent dispensing means comprising:
a single pipette movably supported on said housing; and
a plurality of reagent reservoirs connected to said housing, said single pipette being movable so as to receive the reagent from at least one of said plurality of reagent reservoirs, said pipette being dispensable so as to release the reagent onto said gel plate.

24. The apparatus of claim 23, further comprising:
a washing means positioned on said housing and cooperative with said pipette, said washing means for applying washing water into an interior of said pipette and over an exterior of said pipette; and
an aspirating means positioned on said housing and cooperative with said pipette for aspirating the interior of said pipette to remove the water therefrom.

25. The apparatus of claim 21, said applicator means comprising:
an applicator having a plurality of applicator elements thereon, said applicator being movably positioned on said housing so as to lower said plurality of applicator elements into a corresponding plurality of sample wells formed in said sample plate, said applicator being movable so as to lift said plurality of applicator elements from said plurality of sample of wells.

26. The apparatus of claim 21, said gel plate having electrodes formed thereon, said electrophoresing means comprising:
a power means positioned on said housing, said electrodes of said gel plate being selectively connectable to said power means for applying an electrical field to said gel plate.

27. The apparatus of claim 21, said staining means comprising:
a pipette movably positioned on said housing;
a staining reagent reservoir cooperative with said pipette so as to allow said pipette to be selectively loaded with a staining reagent;
a roller movably positioned on said housing so as to be selectively positionable below said pipette and rollable over said gel plate; and
a washing means positioned on said housing, said washing means for removing the staining reagent from said roller.

28. The apparatus of claim 27, said washing means comprising:
a water container having a water bath therein, said roller being movable so as to submerge within said water bath.

29. The apparatus of claim 21, further comprising:
a drying means positioned on said housing, said drying means for drying the stained gel plate.

30. The apparatus of claim 29, said drying means being an oven dryer.

31. The apparatus of claim 29, said drying means being an air dryer.

32. The apparatus of claim 21, further comprising:
a destaining means positioned on said housing for removing stain from said gel plate.

33. The apparatus of claim 32, said destaining means comprising:
an actuator means positioned on said housing for lowering an edge of the gel plate; and
a water supply means positioned adjacent said actuator means for flowing water across a surface of said gel plate so as to remove the stain therefrom.

34. The apparatus of claim 21, further comprising:
a stacking means positioned at an end of said housing for stacking the gel plate subsequent to scanning by said scanning means.

* * * * *